United States Patent [19]
Kato et al.

[11] Patent Number: 5,713,665
[45] Date of Patent: Feb. 3, 1998

[54] METHOD AND APPARATUS FOR THERMAL DIFFUSIVITY MEASUREMENT

[75] Inventors: Hideyuki Kato; Koichi Nara, both of Tsukuba, Japan

[73] Assignee: Agency of Industrial Science & Technology, Ministry of International Trade & Industry, Tokyo, Japan

[21] Appl. No.: 622,607

[22] Filed: Mar. 26, 1996

[30] Foreign Application Priority Data

May 12, 1995 [JP] Japan ................................. 7-114284

[51] Int. Cl.$^6$ ................................................. G01N 25/20
[52] U.S. Cl. ................................................................ 374/43
[58] Field of Search ................................ 374/43, 44, 31

[56] References Cited

U.S. PATENT DOCUMENTS

| | | | |
|---|---|---|---|
| 3,672,204 | 6/1972 | Green | 374/43 |
| 4,928,254 | 5/1990 | Knudsen et al. | 374/43 |
| 5,044,766 | 9/1991 | Stuart | 374/43 |
| 5,080,495 | 1/1992 | Hashimoto et al. | 374/43 |
| 5,439,291 | 8/1995 | Reading | 374/43 |
| 5,586,824 | 12/1996 | Barkyoumb et al. | 374/44 |

FOREIGN PATENT DOCUMENTS

| | | | |
|---|---|---|---|
| 0213759 | 9/1986 | Japan | 374/43 |
| 0050652 | 3/1987 | Japan | 374/43 |
| 0058242 | 3/1988 | Japan | 374/44 |
| 0071644 | 4/1988 | Japan | 374/43 |
| 0693196 | 10/1979 | U.S.S.R. | 374/44 |
| 1157430 | 5/1985 | U.S.S.R. | 374/44 |

OTHER PUBLICATIONS

Atalla, S.R., et al., "Measurement of Thermal Properties of Liquids with an AC Heated-Wire Technique." Int. Journal of Thermophysics, vol. 2, No. 2, pp. 155–162 (Jan. 1981).

Primary Examiner—Diego F. F. Gutierrez
Attorney, Agent, or Firm—Oblon, Spivak, McClelland, Maier & Neustadt, P.C.

[57] ABSTRACT

A method for thermal diffusivity measurement includes the steps of periodically heating a sample with a heat source modulated at an operating frequency, detecting an ac temperature of the sample at a detection point a predetermined distance apart from a heating point of the sample, the ac temperature being a periodic temperature oscillation, measuring a phase of the detected ac temperature by a phase sensitive detection operation, maintaining the phase constant by controlling the operating frequency of the heat source based on the measured phase to realize a constant-wave-number condition in which both a wave number and a thermal diffusion length are kept constant, and determining the thermal diffusivity of the sample based on the relative change in the operating frequency under the constant-wave-number condition. An apparatus for conducting the method includes a continuous wave laser for locally heating a sample by irradiation with a laser beam, an acoust-optic device for modulating an intensity of the laser beam at an operating frequency and for adjusting a beam spot position on the sample, a thermocouple for detecting an ac temperature of the sample at a detection point a predetermined distance apart from a heating point of the sample, the ac temperature being a periodic temperature oscillation, a lock-in amplifier for measuring a phase of the detected ac temperature by a phase-sensitive detection operation, a computer for calculating an offset between the measured phase and a locked phase, for determining an operating frequency for compensating the phase offset and for outputting the newly determined operating frequency, a chopping driver for working the acoust-optic device in response to the operating frequency based on the computer output, and means for determining the thermal diffusivity of the sample based on the relative change in the operating frequency which keeps the locked phase constant to realize a constant-wave-number condition in which both a wave number and a thermal diffusion length are kept constant.

2 Claims, 1 Drawing Sheet

METHOD AND APPARATUS FOR THERMAL DIFFUSIVITY MEASUREMENT

BACKGROUND OF THE INVENTION

1. Field of the Invention

This invention relates to a method and an apparatus for thermal diffusivity measurement, more particularly to a method for thermal diffusivity measurement based on ac calorimetry in which a sample is periodically heated and its thermal diffusivity is determined by measuring the propagating properties of the thermal waves in the sample periodically heated, and an apparatus for conducting the method.

2. Description of the Prior Art

In the development of high-temperature superconducting materials and other new materials, only minute amounts of high-quality material can ordinarily be synthesized in the early stages. Since measurement utilizing ac calorimetry enables high-sensitivity evaluation of thermal properties even with respect to extremely small quantities of material, it has therefore been considered optimum for evaluating such new materials. This has led to the development of various measurement technologies based on ac calorimetry, including methods for measuring specific heat, thermal diffusivity and thermal conductivity.

Although numerous thermal diffusivity measurement methods have been reported, they all fall into the following two main categories (where A is the amplitude and $\theta$ is the phase of the sample ac temperature in response to periodic heating at operating frequency f, and l is the characteristic distance between the heat source and the detection point).

(1) In the case where distance l is constant, the thermal diffusivity D is determined based on measurement of the dependence of the amplitude A or the phase $\theta$ on the operating frequency f.

(2) In the case where operating frequency f is constant, the thermal diffusivity D is determined based on measurement of the dependence of the amplitude A or the phase $\theta$ on the distance l.

However, determination of the temperature dependence of the thermal diffusivity D by either method (1) or (2) requires the complicated work of repeating the aforesaid measurement with respect to the sample at every temperature. Since a variation in temperature may easily change the magnitude of the thermal diffusivity D by one or two orders of ten, moreover, precise temperature control is necessary. A great amount of time is therefore generally required for acquiring detailed data over a wide temperature range.

The method (2), in which the operating frequency f is fixed, has the further drawback that the intrinsically narrow dynamic range of thermal diffusivity D measurement tends to lead to inclusion of system noise in the results if the measurement is conducted over a wide range.

In addition, while the method (1) requires the operating frequency f to cover a broad range, this makes it difficult to achieve high resolution because the signal strength falls off sharply on the high-frequency side.

This invention was accomplished in light of the foregoing problems and aims at providing a method and an apparatus for thermal diffusivity measurement which enable measurement of thermal diffusivity to be conducted efficiently with high precision and high resolution.

SUMMARY OF THE INVENTION

For achieving this object, the invention provides a method for thermal diffusivity measurement comprising the steps of:

periodically heating a sample with a heat source modulated at an operating frequency, detecting an ac temperature of the sample at a detection point a predetermined distance apart from a heating point of the sample, the ac temperature being a periodic temperature oscillation, measuring a phase of the detected ac temperature by a phase sensitive detection operation, maintaining the phase constant by controlling the operating frequency of the heat source based on the measured phase, to realize a constant-wave-number condition in which both a wave number and a thermal diffusion length are kept constant; and determining the thermal diffusivity of the sample based on the relative change in the operating frequency under the constant-wave-number condition.

The invention further achieves its object by providing an apparatus for thermal diffusivity measurement comprising:

a continuous wave laser for locally heating a sample by irradiation with a laser beam, an acoust-optic device for modulating an intensity of the laser beam at an operating frequency and for adjusting a beam spot position on the sample, a thermocouple for detecting an ac temperature of the sample at a detection point a predetermined distance apart from a heating point of the sample, the ac temperature being a periodic temperature oscillation, a lock-in amplifier for measuring a phase of the detected ac temperature by a phase-sensitive detection operation, a computer for calculating an offset between the measured phase and a locked phase, the determining an operating frequency for compensating the phase offset and for outputting the newly determined operating frequency, a chopping driver for working the acoust-optic device in response to the operating frequency based on the computer output, and means for determining the thermal diffusivity of the sample based on the relative change in the operating frequency which keeps the locked phase constant to realize a constant-wave-number condition in which both a wave number and a thermal diffusion length are kept constant.

As set out in the foregoing, in this invention the sample is first periodically heated at the operating frequency and the operating frequency is feedback controlled to maintain the phase of the ac temperature produced by the heat source constant. If the sample temperature is changed, the phase of the measured ac temperature tends to change in response to the change in the thermal diffusivity. Owing to the feedback control, however, the operating frequency of the heat source is immediately controlled in response to the change in the phase, thereby maintaining the phase constant.

Since the invention detects the thermal diffusivity by using the relative change in the operating frequency in place of the relative change in the thermal diffusivity in this manner, the thermal diffusivity of the sample can be continuously measured even if the temperature of the sample is swept. Since the thermal diffusion length can be locked constant during the whole measurement, moreover, it can be ascertained with high accuracy.

The above and other features of the present invention will become apparent from the following description made with reference to the drawings.

DESCRIPTION OF THE PREFERRED EMBODIMENT

Figure 1:
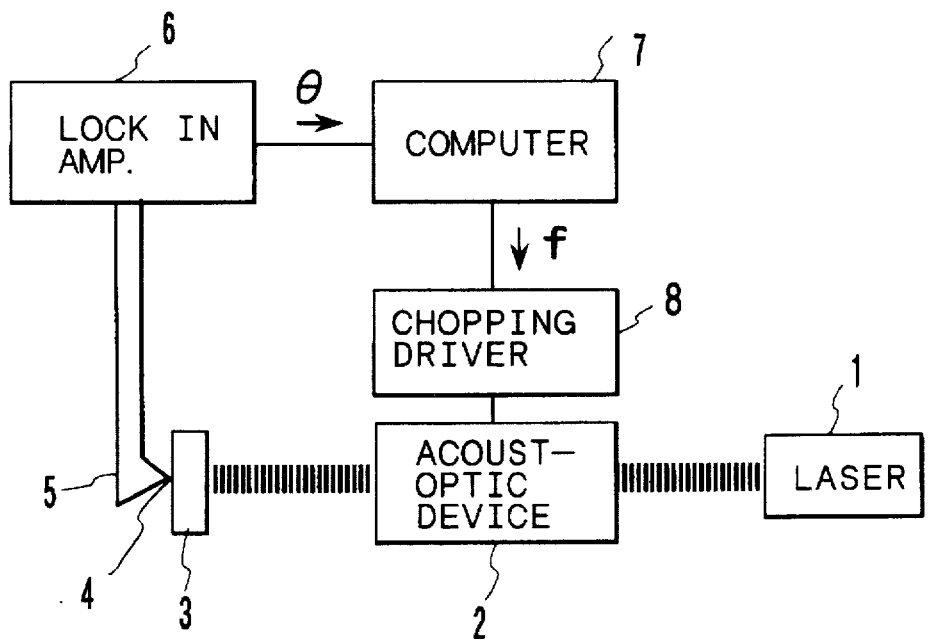
FIG. 1 is a block diagram of an embodiment of the apparatus for thermal diffusivity measurement according to the invention.

FIG. 1 is a block diagram showing an embodiment of the apparatus for thermal diffusivity measurement for implementing the method of the present invention. This measurement apparatus utilizes a He-Ne laser 1 as the light source of its optical heating system. The laser beam output from the He-Ne laser 1 is passed and modulated through an acoust-optic device 2 and is irradiated onto the surface of a thin-plate sample 3 of thickness d to form a beam spot of gaussian intensity profile which periodically heats the irradiated portion. As a result, the temperature at a detection point 4 on the surface of the sample 3 oscillates periodically. This periodic temperature oscillation (ac temperature) is detected by a thermocouple 5 and lock-in detected by a lock-in amplifier 6 to determine its phase θ. The error between the so-determined phase θ and a fixed control value is constantly monitored by a computer 7, which determines an operating frequency f for compensating the error. The operating frequency f determined by the computer 7 is used to control the acoust-optic device 2 through a chopping driver 8. Owing to this control of the acoust-optic device 2, the intensity of the laser beam from the He-Ne laser 1 is modulated at a prescribed operating frequency f and constantly directed to a specified position on the surface of the sample 3.

Measurement is possible with respect to any sample insofar as it is a substance exhibiting a thermal diffusivity within the ordinary range. If the sample is transparent and cannot be heated by light, its surface is blackened by treatment with carbon black or the like.

The sample is prepared to have a thickness of about 10 μm–1.0 mm and the detection point 4 is located on its rear side relative to the point of beam incidence. While the output power of the laser constituting the heat source is appropriately selected based on the material and thickness of the sample, it is typically in the range of 1–10 mW.

In the case of a thermally isotropic material, the diameter σ of the laser beam directed onto the sample can be selected independently of the ratio σ/d of the diameter σ to the sample thickness d. In the case of a thermally anisotropic material, however, it is preferable to select the beam diameter σ such that σ/d>>10.

As regards the locked phase mentioned above, it is preferable for the ratio d/λ of the sample thickness d to the thermal diffusion length λ (the invasion depth of the temperature variation) to be in the approximate range of 2–3.5. When the d/λ is smaller than 2, the measurement is likely to include error, while when it is larger than 3.5, accurate measurement becomes difficult owing to the small magnitude of the signal.

The value of the phase to be fixed is selected so that the thermal diffusion length λ is around ⅓ of thickness d.

The modulation frequency of the beam directed onto the sample is the operating frequency which gives the aforesaid phase to be fixed and is ordinarily selected within the range of from 0.1 Hz to 1 kHz as appropriate for the thermal diffusivity and thickness of the sample.

In the illustrated embodiment, a laser is used as an example of the means for heating the sample. Instead, however, the periodic heating of the sample can also be conducted by using an electric ac power source to pass square or sine wave pulses through a film-like resistance heater applied over the entire surface of the sample. The aforesaid control of the heating frequency can be easily conducted using a prior art device.

The apparatus for thermal diffusivity measurement thus includes a feedback loop through which the operating frequency f is feedback controlled so as to maintain the phase θ of the periodic temperature oscillation at the detection point 4 on the rear surface of the sample 3 constant irrespective of changes in the sample temperature.

Moreover, the use of the acoust-optic device 2 and the chopping driver 8 as the means for controlling the operating frequency enable the control to be implemented quickly and accurately.

The method for thermal diffusivity measurement according to the invention will now be explained.

The thermal diffusivity measurement method of this invention uses the operating frequency f as a measurement variable and feedback controls the operating frequency f so as to cancel out any change of the thermal diffusivity D, thereby enabling the thermal diffusivity D to be detected by replacing it with the operating frequency f. This will be explained in the following based on thermal wave propagation equation.

The propagation of a thermal wave produced by a ρc·exp(i2πft) point heat source (where ρ is density and c is heat capacity per unit volume) can be generally expressed in terms of the ac temperature $T_{ac}$ at a point located distance l from the point heat source as $$T_{ac}(4\pi Dl)^{-1} \cdot exp\{-kl+i(2\pi ft-kl)\} \qquad \text{(Eq. 1)}.$$

The wave number k of the thermal waves characterizing this is expressed by $$k=(\pi f/D)^{1/2}=\lambda^{-1} \qquad \text{(Eq. 2)},$$

where λ is the thermal diffusion length.

As can be seen from Eq. 1, the phase of the detected ac temperature $T_{ac}$ is $-kl$ and depends solely on the wave number k under conditions where distance l is constant. From Eq. 2, moreover, it follows that wave number k depends solely on the thermal diffusivity D and the operating frequency f.

Assume that a shift occurs from a state in which the frequency is f1, the sample temperature at measurement is T1, the thermal diffusivity is D1 and the wave number is k1 to one in which the frequency is f2, the sample temperature at measurement is T2, the thermal diffusivity is D2 and the wave number is k2.

If the frequency f2 is set so that wave number k2 equals wave number k1, it follows from Eq. 2 that $$f1/D1=f2/D2 \text{ or } f2/f1=D2/D1 \qquad \text{(Eq.3)}$$

A change in the sample temperature T is accompanied by a change in the thermal diffusivity D. When the aforesaid feedback loop is in effect, therefore, the operating frequency f is changed to balance the loop as shown in Eq. 3. In other words, the change in the thermal diffusivity D is detected by replacing it with the change in the operating frequency f, thereby enabling the relative change D2/D1 in the thermal diffusivity D to be detected as replaced by the relative change f2/f1 in the operating frequency.

Figure 2:
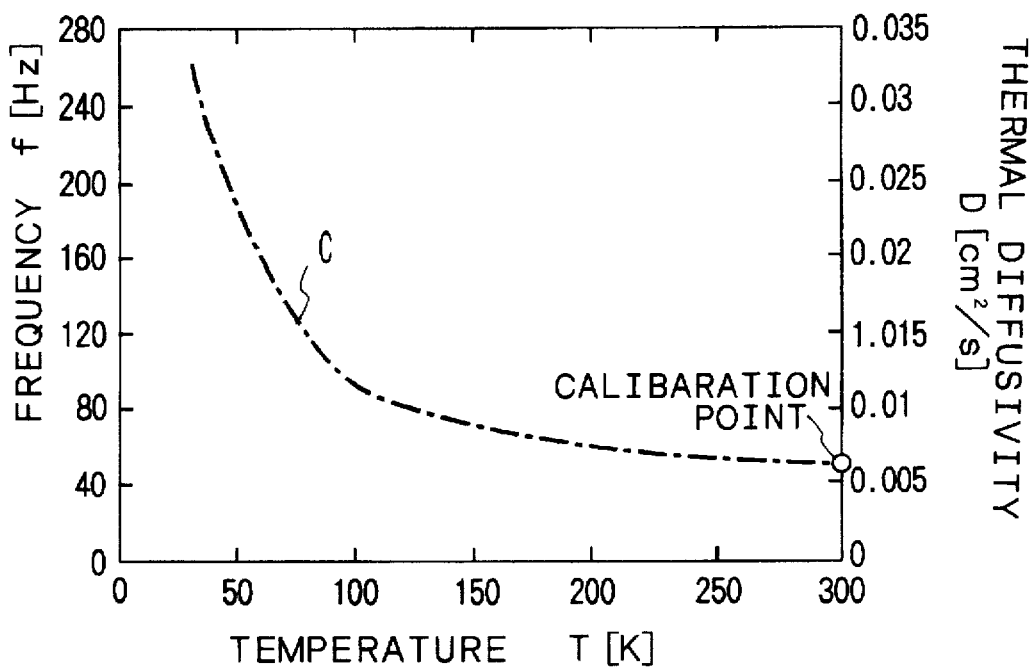
FIG. 2 is a graph showing measurement results obtained by the method for thermal diffusivity measurement according to the invention.

FIG. 2 is a graph showing measurement results obtained by the method for thermal diffusivity measurement according to this invention. A high-temperature superconducting material was used as the sample. The curve C in this graph shows the operating frequency f at different values of the sample temperature T when the sample was varied from an extremely low temperature to around normal room temperature. The thermal diffusivity D of the sample can be calculated from the curve C of the operating frequency f as described in the following.

Define the operating frequency when the aforesaid feedback control is conducted at a temperature T1 on the very low temperature side as f1 and the operating frequency when the feedback is conducted at normal room temperature Ts as fs. As the thermal diffusivity Ds of the sample at normal room temperature Ts (the calibration point ○ in the graph) use a known value obtained from, for example, the measured operating frequency f dependence of the phase θ. Defining the thermal diffusivity at temperature T1 as D1, it follows from Eq. 3 that D1/Ds=f1/fs during the aforesaid feedback control. The thermal diffusivity D1 can therefore be obtained from the relative change in the operating frequency f1/fs as (f1/fs)·Ds. In this way, the thermal diffusivity D at different sample temperatures T can be obtained for every point on the curve C.

In the specific case shown in FIG. 2, at 100 K the operating frequency was approximately 100 Hz and the thermal diffusivity was approximately 0.012 $cm^2$/s, while at 200 K the operating frequency was approximately 65 Hz and the thermal diffusivity was approximately 0.008 $cm^2$/s.

The sample is small and its temperature is assumed to reach the ambient temperature in a very short time. Since the sample temperature T can therefore be stably maintained, the operating frequency f at each sample temperature T rapidly stabilizes and can be quickly determined. As a result, the thermal diffusivity D can also be rapidly determined under temperature scanning within the range in which the feedback control loop stays in balance. The efficiency of data acquisition is ten or more times that of the prior-art methods.

In addition, since the thermal diffusion length λ (the wave number k of the thermal waves) is maintained constant, it is possible to establish steady measurement conditions that minimize systematic error and enable the thermal diffusivity D to be determined with high accuracy.

Further, since the optimum operating frequency f can be constantly established in response to change in the thermal diffusivity D with the sample temperature T, a wide dynamic range and high resolution can be maintained.

Although the heat source was stated to be a point heat source in the foregoing explanation, even in the case of a heat source having a finite spread, the detected ac temperature T can ultimately be generally expressed as $$T = A \cdot \exp\{i(2\pi ft + \theta)\} \quad \text{(Eq. 4)}$$

since such a heat source can be analyzed as a superposition of point heat sources. If all of the geometrical conditions (sample shape, heat-source intensity profile, relationship between heating position and detecting position, and thermal diffusion length) are maintained constant, the phase θ is maintained constant as a result. Since the conditions other than the thermal diffusion length are almost completely independent of the sample temperature, however, maintaining the phase θ constant can be considered equivalent to maintaining the thermal diffusion length, i.e., the wave number, constant. Eq. 3 can therefore be utilized and the thermal diffusivity can be measured by the method for thermal diffusivity measurement according to this invention irrespective of the heat source adopted.

As explained in the foregoing, since the method for thermal diffusivity measurement of this invention feedback controls the operating frequency to maintain the phase of the ac temperature constant and determines the thermal diffusivity based on the relative change in the operating frequency at each instant, and, moreover, since the sample temperature T can be stabilized very rapidly, the thermal diffusivity D can be rapidly determined under temperature scanning within the range in which the feedback control loop stays in balance, whereby data acquisition can be achieved at an efficiency that is ten or more times that of the prior-art methods.

The fact that the phase of the ac temperature is maintained constant further makes it possible to establish steady measurement conditions that minimize systematic error and enable the thermal diffusivity to be determined with high accuracy.

When a laser beam is used as the heating light source, moreover, the frequency of the beam intensity modulation can be easily controlled by using an acoust-optic device that ingeniously utilizes Bragg diffraction. Without any moving mechanical portions, this device exhibits a wide dynamic range and a rapid response which together enable the operating frequency to be constantly adjusted to the optimum value in response to changes in the thermal diffusivity with sample temperature. It therefore becomes possible to obtain accurate measurement values and maintain a broad dynamic range and high resolution.

What is claimed is:

1. A method for thermal diffusivity measurement comprising the steps of:

periodically heating a sample with a heat source modulated at an operating frequency, detecting an ac temperature of the sample at a detection point a predetermined distance apart from a heating point of the sample, the ac temperature being a periodic temperature oscillation, measuring a phase of the detected ac temperature by a phase sensitive detection operation, maintaining the phase constant by controlling the operating frequency of the heat source based on the measured phase to realize a constant-wave-number condition in which both a wave number and a thermal diffusion length are kept constant, and determining the thermal diffusivity of the sample based on the relative change in the operating frequency under the constant-wave-number condition.

2. An apparatus for thermal diffusivity measurement comprising:

a continuous wave laser for locally heating a sample by irradiation with a laser beam, an acoust-optic device for modulating an intensity of the laser beam at an operating frequency and for adjusting a beam spot position on the sample, a thermocouple for detecting an ac temperature of the sample at a detection point a predetermined distance apart from a heating point of the sample, the ac temperature being a periodic temperature oscillation, a lock-in amplifier for measuring a phase of the detected ac temperature by a phase-sensitive detection operation, a computer for calculating an offset between the measured phase and a locked phase, for determining an operating frequency for compensating the phase offset and for outputting the newly determined operating frequency, a chopping driver for working the acoust-optic device in response to the operating frequency based on the computer output, and means for determining the thermal diffusivity of the sample based on the relative change in the operating frequency which keeps the locked phase constant to realize a constant-wave-number condition in which both a wave number and a thermal diffusion length are kept constant.

* * * * *